United States Patent [19]

Frishberg

[11] 4,225,719
[45] Sep. 30, 1980

[54] PROCESS FOR PREPARING 2-AMINO-5-FORMYLTHIAZOLE AND ITS HYDROBROMIDE SALT

[75] Inventor: Mark D. Frishberg, Kingsport, Tenn.

[73] Assignee: Eastman Kodak Company, Rochester, N.Y.

[21] Appl. No.: 974,285

[22] Filed: Dec. 29, 1978

[51] Int. Cl.² .......................................... C07D 277/20
[52] U.S. Cl. .................................................. 548/194
[58] Field of Search .................. 260/306.8 R; 548/194

[56] References Cited

U.S. PATENT DOCUMENTS 2,468,401  4/1949  King et al. .................... 260/306.6 R
3,933,838  1/1976  Manghisi ....................... 260/306.8 R

FOREIGN PATENT DOCUMENTS 1182234  11/1964  Fed. Rep. of Germany.

Primary Examiner—Nicholas S. Rizzo
Attorney, Agent, or Firm—Donald W. Spurrell; Daniel B. Reece, III

[57] ABSTRACT

Process for the preparation of 5-formyl-2-aminothiazole hydrobromide and 2-amino-5-formylthiazole which comprises reacting bromomalonaldehyde and thiourea in the substantial absence of acid or base to form the 5-formyl-2-aminothiazole hydrobromide, and then treating the same with base to form the aminothiazole.

4 Claims, No Drawings

PROCESS FOR PREPARING 2-AMINO-5-FORMYLTHIAZOLE AND ITS HYDROBROMIDE SALT

This invention relates to a novel process for preparing 2-amino-5-formylthiazole (AFT) and its hydrobromide salt in very high yields, compared to previously known processes.

The preparation of AFT by the reaction of chloromalonaldehyde and thiourea in refluxing sodium bisulfite solution is disclosed in Example 8 of German Pat. No. 1,182,234, but the desired product was obtained in a very low yield. Moreover, a duplication of that example using the more readily available bromomalonaldehyde gave only a resinous material which mass spectrometry showed to contain no AFT.

The synthesis of AFT by treating chloromalonaldehyde with thiourea is 50% aqueous acetic acid is described on page 378 of Volume 12 of the Journal of Medicinal Chemistry as giving about a 30% crude yield. Repeating that procedure using bromomalonaldehyde also gave AFT in only about a 30% crude yield.

I have discovered that AFT hydrobromide can be prepared with yields in excess of about 80% by reacting bromomalonaldehyde and thiourea at relatively low—ambient or below—or at elevated temperatures, in the substantial absence of acids or bases, and preferably in a nitrogen atmosphere. The term "substantial absence" means that no acids or bases, or the like are added to control pH or to perform other chemical functions. The present reaction system, in other words, is greatly simplified over the prior art and the reactions are allowed to proceed unencumbered. It is noted, however, that the present invention can tolerate small amounts of such acids or bases or the like which may find their way into the system as impurities or the like, without seriously reducing the greatly improved yields. The product which is initially formed is the AFT hydrobromide salt which can be converted to the free amine by treating the former with a base such as ammonium hydroxide, sodium hydroxide, sodium bicarbonate, sodium carbonate, potassium hydroxide or the like. The present process is preferably carried out in water but other inert solvents including aqueous alcohols such as 50/50 by volume aqueous solutions of methanol, ethanol or isopropanol can be employed although their use does not offer any particular advantages.

The temperature at which the present process can be carried out can be varied rather widely although low temperatures require excessive reaction times and high temperatures, e.g., above about 100° C. may decompose the product. Preferably, the process is carried out at a temperature in the range of from about 15° C. to about 100° C., and most preferably between about 20° C. and 50° C. The use of a nitrogen atmosphere is preferred.

The bromomalonaldehyde can be prepared by known procedures such as disclosed in the Journal of Organic Chemistry, 28, 3243, for example, by treating a dilute hydrochloric acid solution of malonaldehyde tetramethyl acetal with bromine at below 35° C. AFT and its hydrobromide salt can be used in the synthesis of azo dyes such as the 5-formyl-2-thiazolylazo dyes disclosed in U.S. Pat. No. 3,829,410.

My novel process is further illustrated by the following examples.

EXAMPLE 1

Bromomalonaldehyde (142 g, 0.94 m) was suspended in 750 ml of water under nitrogen and thiourea (71.5 g, 0.94 m) was added with stirring. A very slight exotherm was noted and a homogeneous yellow solution was obtained in five to ten minutes. After stirring at a temperature of about 20°–25° C. for 3 days, the mixture containing 5-formyl-2-aminothiazole hydrobromide was poured onto ice and neutralized with concentrated $NH_4OH$. The orange-red product, 5-formyl-2-aminothiazole, was collected by filtration, washed with cold water, and air dried to yield 77 g (0.6 m, 64%) of product. Additional product was obtained by concentrating the filtrates for a total yield of 106 g (0.83 m, 88%). The crude product was used for the preparation of azo dyes without further purification. The product can be recrystallized from hot water if desired to give gold needles, mp 165°–166.5° C. (uncorrected); see Vol. 12, p. 378, Journal of Medicinal Chemistry, giving mp of 160°–167° C. (melting with decomposition and resolidification after gradually darkening above 140° C.).

EXAMPLE 2

4.5 Grams (0.03 m) of bromomalonaldehyde and 2.28 g (0.03 m) of thiourea were added to 25 ml of $H_2O$ and heated on a steam bath. The solution was homogeneous before heat was applied and the color changed from yellow to orange-brown shortly after heating began. No change occurred in TLC (90/10 $CHCl_3/CH_3OH$) between 2 hours and 3 hours and the reaction was essentially complete by that time. After 3 hours, the reaction system was filtered hot, cooled and neutralized with concentrated $NH_4OH$, and the product collected, washed with $H_2O$ and air dried. The yield was 2.26 g of red-brown microcrystalline powder (0.0177 m, 59%). It is noted that in this preparation there was no attempt to maximize yield via concentration of filtrate, nitrogen blanket, or the like.

The invention has been described in detail with particular reference to preferred embodiments thereof, but it will be understood that variations and modifications can be effected within the spirit and scope of the invention.

I claim:

1. Process for the preparation of 5-formyl-2-aminothiazole hydrobromide which comprises reacting bromomalonaldehyde and thiourea in the substantial absence of added acids or bases.

2. Process according to claim 1 for the preparation of 5-formyl-2-aminothiazole wherein the hydrobromide is treated with base.

3. Process according to claim 1 wherein the reaction is carried out in water at a temperature of about 15° C. to about 100° C.

4. The process of claim 3 wherein the reaction is carried out under a nitrogen atmosphere at a temperature of from about 20° C. to about 50° C.

* * * * *